(12) United States Patent
Warlick (10) Patent No.: US 8,778,414 B2
(45) Date of Patent: Jul. 15, 2014

(54) APPARATUS AND METHOD FOR CELLULAR EXTRACT ENHANCEMENT

(75) Inventor: John Warlick, Woodstock, GA (US)

(73) Assignee: General Patent, LLC, Marietta, GA (US)

( * ) Notice: Subject to any disclaimer, the term of this patent is extended or adjusted under 35 U.S.C. 154(b) by 1527 days.

(21) Appl. No.: 11/836,532

(22) Filed: Aug. 9, 2007

(65) Prior Publication Data
US 2009/0041864 A1  Feb. 12, 2009

(51) Int. Cl.
| A61K 36/00 | (2006.01) |
| A23L 1/28 | (2006.01) |
| A23L 2/00 | (2006.01) |
| A23L 1/30 | (2006.01) |
| A23F 5/36 | (2006.01) |
| A23F 3/18 | (2006.01) |
| A23F 5/26 | (2006.01) |
| A23L 2/38 | (2006.01) |
| C12C 3/08 | (2006.01) |

(52) U.S. Cl.
CPC ............... *A61K 36/00* (2013.01); *A23L 1/3002* (2013.01); *A23F 5/36* (2013.01); *A23F 3/18* (2013.01); *A23F 5/26* (2013.01); *A23L 2/38* (2013.01); *C12C 3/08* (2013.01)
USPC ............. 424/725; 426/425; 426/590; 99/278; 99/288; 99/290

(58) Field of Classification Search
None
See application file for complete search history.

(56) References Cited

U.S. PATENT DOCUMENTS

| 2,816,031 | A | * | 12/1957 | Specht et al. .................... 426/16 |
| H6730000 | | | 9/1989 | Hullah et al. |
| 4,983,408 | A | | 1/1991 | Colton |
| 5,436,023 | A | | 7/1995 | Avera |
| 5,939,121 | A | | 8/1999 | Gutwein et al. |
| 6,405,637 | B1 | * | 6/2002 | Cai .................................. 99/293 |
| 6,669,979 | B1 | | 12/2003 | Zhao et al. |
| 6,726,947 | B1 | | 4/2004 | Gutwein et al. |
| 6,968,775 | B2 | | 11/2005 | Burrows et al. |
| 7,017,473 | B2 | | 3/2006 | Mazzola, Jr. et al. |
| 7,040,218 | B1 | | 5/2006 | Biolchini, Jr. |
| 7,225,728 | B2 | | 6/2007 | Lyall, III |
| 7,228,066 | B2 | | 6/2007 | Pope |
| 2005/0150830 | A1 | * | 7/2005 | Laugharn et al. ............. 210/634 |

FOREIGN PATENT DOCUMENTS

RU        2038110 C1  *  6/1995

* cited by examiner

*Primary Examiner* — Qiuwen Mi
(74) *Attorney, Agent, or Firm* — David L King (57) ABSTRACT

An apparatus 110 for increasing extracts 100E taken from cellular plant tissue 100 has a preparation container 114 for holding the cellular plant tissue 100, the container 114 having an inlet or opening 112 to receive a fluid 101 to wet the cellular plant tissue 100 and take extracts 100E from the cellular plant tissue 100 to create a fluid with extracts mixture 101E, and an outlet to pass the fluid with extracts mixture, a lower portion of the container is a holding vessel 111 to receive the fluid with extracts 101E; and an acoustic shock wave device 43 for transmitting shock waves 200 to the wet cellular plant tissue 100 to enhance release of extracts 100E into the fluid 101. The invention further discloses a method of increasing extracts 100E taken from cellular plant tissue 100 comprises the steps of placing prepared cellular plant tissue 100 in a container 114; introducing a fluid 101 into the container 114 to wet and immerse the prepared cellular plant tissue 100; and emitting acoustic shock waves 200 into the fluid 101 immersed cellular plant tissue 100 to increase the extracts 100E released by the plant tissue 100 into the fluid 101 and a product made from the method, the product being a beverage, medicine or drug.

12 Claims, 10 Drawing Sheets

APPARATUS AND METHOD FOR CELLULAR EXTRACT ENHANCEMENT

TECHNICAL FIELD

The present invention relates to equipment and methods to enhance the amount or percentage of extractable material from cellular plant products such as coffee beans, tea leaves, wheat, barley, oats, hops, nuts, more particularly to the use of acoustic shock waves to facilitate extract yields.

BACKGROUND OF THE INVENTION

Many beverage products employ plant products in their preparation. These plant products are typically prepared in a variety of ways to maximize the yields or percentage of extractable material that can be used to make the beverage. The plant material is often dried, then roasted and flaked or ground into particle or powders prior to being heated in a liquid, normally water to make a beverage, which can be served hot or served chilled or even room temperature.

Beer and other alcohol based beverages use a process of fermentation to achieve the desired alcohol content. A variety of combinations of barley, hops and wheat or oats or rice can be used to make such products. Typically the plant products are cooked to a boil to achieve the right consistency of flavor and taste, the recipes of such drinks are often closely guarded secrets.

The most favorite beverages using plant products are coffee and tea. In coffee, the fruit seed of a coffee plant is harvested, this seed commonly referred to as the coffee bean is used to make a beverage with a 400 billion cup per year consumption worldwide.

Tea employs the leaf of tea plants to make a beverage that is second only to coffee in consumption.

Both of these drinks are made using either the dried roasted ground bean in the case of coffee or dried finely chopped tea leaves in the preparation of tea. In each case very hot water is used to wash extracts from the plant material to create the beverage. The cellular fiber or residue is isolated from the beverage by various means most commonly filtration.

The use of various types of beans or blends of such beans and the amount of preparation such as the degree of roasting can greatly alter the flavor and aroma of the coffee. Similarly teas of different blends or mixtures of leaves can alter the taste of the finished product.

Recently, the beneficial aspects of coffee and tea have been shown. A variety of ingredients or compositions that help prevent a variety of diseases are locked up in the cellular tissue of tea leaves and coffee beans. In U.S. Pat. No. 6,669,979 sodium bicarbonate is used to create a spike in polyphenols in coffee. The polyphenols simply do not adequately dissolve in the hot water alone. This polyphenolic fraction isolated from the coffee brew has been shown to inhibit a chemical tumor promoter which caused oxidative stress and inflammatory response in mice. In the case of coffee, typically only a small percentage of these nutrients can be extracted. In particular, the coffee bean grounds are encased in an oil crushed from the bean pulp, the oil is hydrophobic and prevents water from effectively penetrating the cellular fibers. Heating the water helps break down this oil, but at best only 10-15% of the extractables are released into the water. This means four to five the times the amount of coffee grounds must be used to make a coffee beverage based on these very low yields.

It has been reported in U.S. Pat. No. 7,228,066 that agitating the grounds by pulsing a fluid spray improves wetting of the coffee material and the agitation helps break down the oils coating the grounds and this helps improve the yield slightly. A stirring coffee press is disclosed in U.S. Pat. No. 7,040,218 that has a rotatable blade to stir the coffee grounds while simultaneously compressing and agitating the grounds. U.S. Pat. No. 7,227,728 shows a brewing apparatus with a pre-infusion and pulse brewing of water into the grounds to create turbulence that jostles and promotes more uniform brewing.

The present invention provides a new way to unlock the flavors and nutrients in coffee, teas and other plant based beverages. The present invention's ability to change the plant or seed's cellular tissue response to the water can result in a higher effective yield of extracts deliverable to the beverage than was heretofore possible.

SUMMARY OF INVENTION

An apparatus for increasing extracts taken from cellular plant tissue has a preparation container for holding the cellular plant tissue, the container having an inlet or opening to receive a fluid to wet the cellular plant tissue and take extracts from the cellular plant tissue to create a fluid with extracts mixture, and an outlet to pass the fluid with extracts mixture, a holding vessel to receive the fluid with extracts; and an acoustic shock wave device for transmitting shock waves to the wet cellular plant tissue to enhance release of extracts into the fluid.

The apparatus may also include a heating element to heat the fluid prior to contacting the cellular plant tissue and a means to separate the fluid and extracts mixture from the cellular tissue wherein the cellular tissue is mechanically held as the fluid with extracts mixture passes to the holding vessel.

Preferably the acoustic shock wave device transmits the shock waves in a pattern covering a volumetric region of the held cellular tissue as the cellular tissue is immersed in the fluid. The acoustic shock wave pattern is transmitted at least initially as the fluid passes through the cellular tissue. Preferably the acoustic shock wave pattern is transmitted continuously as the fluid passes through the cellular tissue. Alternatively, the transmission of the acoustic shock wave pattern is pulsed intermittently as the fluid passes through the cellular tissue.

The cellular plant tissue can be ground coffee and the apparatus is coffee maker or coffee brewer, or the cellular plant tissue is coffee beans placed in a slurry to create a fluid with extract mixture to make an instant coffee product. Also, the cellular plant tissue can be made of tea leaves and the apparatus is a tea maker. Additionally, the cellular plant tissue is one or more of the following: hops, barley, wheat, oats, soy beans or rice and the apparatus is used in brewing a beverage having an alcohol content. The cellular plant tissue can be used in the formulation of an extract for use in a drug or medicine composition.

The invention further discloses a method of increasing extracts taken from cellular plant tissue comprises the steps of placing prepared cellular plant tissue in a container; introducing a fluid into the container to wet and immerse the prepared cellular plant tissue; and emitting acoustic shock waves into the fluid immersed cellular plant tissue to increase the extracts released by the plant tissue into the fluid and a product made from the method, the product being a beverage, medicine or drug.

DEFINITIONS

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"Embryo" a discrete mass of cells with a well defined structure that is capable of growing into a whole plant.

"Extracorporeal" occurring or based outside the living body or plant structure.

"Extract" to obtain something from a source, usually by separating it out from other material.

A "generalized paraboloid" according to the present invention is also a three-dimensional bowl. In two dimensions (in Cartesian coordinates, x and y) the formula $y^n=2px$ [with n being ≠2, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

"Ovule" The body which, after fertilization, becomes the seed.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100 ns. The duration of a shock wave is typically below 1-3 micro-seconds (μs) for the positive part of a cycle and typically above some microseconds for the negative part of a cycle.

"seed" The ripened ovule, consisting of the embryo and its proper coats.

'Waves/wave fronts" described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

In US 2006/0100551, published May 11, 2006 it was discovered that plant tissue could be stimulated with low energy acoustic shock waves. In that study old seeds that typically would not germinate were treated with non cell damaging acoustic shock waves and planted. A surprisingly high percentage of the seeds propagated and grew into full sized plants.

It was recognized that such a use of acoustic shock waves would be very helpful in plant cell growth and stimulation as long as the acoustic waves were not of sufficiently high energy to cause cell rupture or damage.

The present invention employs acoustic shock waves to bombard cellular plant tissue used in preparation of beverages or medicines wherein an extract of the plant tissue is used to make the beverage or medicine. The objective is to release as much of the nutrients or compounds in the cellular tissue as possible. Therefore, the acoustic wave pattern is primarily interested in exposing each particle of the plant tissue to the acoustic waves. Cell damage via a mechanical rupturing of the cell walls can be useful in some applications because the object is to release the nutrients contained in the cells. In other applications cell rupturing may not be desirable and the present invention can still increase extract yields without mechanical rupturing of the outer cell walls if required. The release of the nutrients can even be improved by exposure to the shock waves at low energy due to the vibrational response of the cell walls which enables the contained nutrients to migrate across the wall as well as the agitation of the plant tissue causing a mechanical impacting of the plant tissue particles helping to enable the fluid, normally hot water to penetrate the surface of the grounds in the case of brewing coffee. This remarkable ability of acoustic shock waves to increase the permeability of the cell walls and linings holding nutrients was first discovered in early uses of acoustic waves in medical treatments. The acoustic shock wave has a very rapid pressure spike achieved in an extremely short duration accordingly as the wave approaches a cell it compresses the cell initially, thereafter the pressure of the wave drops in a slower fashion as it continues across the cell that tends to put tension on the cell wall as it relaxes from the sudden compressive rise in pressure. Therefore the cell wall rebounds in a spring like fashion and stretches slightly increasing permeability. Rapid bombardment of the acoustic waves in a pattern sequence first compressing then stretching creates a rapid cellular squeezing effect enhancing permeability into and out of the cell walls.

The acoustic wave pattern is best transmitted to the cellular plant tissue when the plant tissue is fully immersed in fluid. Air pockets and voids must be avoided as those will stop the waves from propagating through the medium, in this case the fully immersed plant tissue.

One important aspect of the present invention is that the wave pattern should be such that any volumetric focal region should be large enough to impinge all the plant cells. Accordingly the highly focused wave pattern that converges to a point of high energy is only useful to the extent the adjacent cells are sufficiently exposed to acoustic energy.

To insure a large enough band of acoustic shock wave energy is transmitted to all targeted plant tissue, the use of spherical waves, unfocused waves or planar waves or near planar waves can be used or convergent or divergent wave patterns having the targeted region pre or post convergent. Alternatively the focal volume region can be enlarged to a volume large enough to encompass all of the immersed cellular plant tissue held in the container. In these ways the release of plant nutrients into the fluid is greatly enhanced.

The present invention relates to the use of various pressure pulse wave patterns or acoustic shock wave patterns as illustrated in FIGS. 1-12 for stimulating plant cellular tissue release of extracted nutrients and compounds. Each illustrated wave pattern will be discussed later in the description; however, the use of each has particularly interesting beneficial features that are a remarkably valuable new tool in the effort to increase plant cellular tissue extract and production. For purposes of illustration an exemplary apparatus employing the present invention is described. Those skilled in the art will appreciate the concepts as shown are equally applicable to other devices used in manufacturing other beverages and medicines.

Figure 13A:
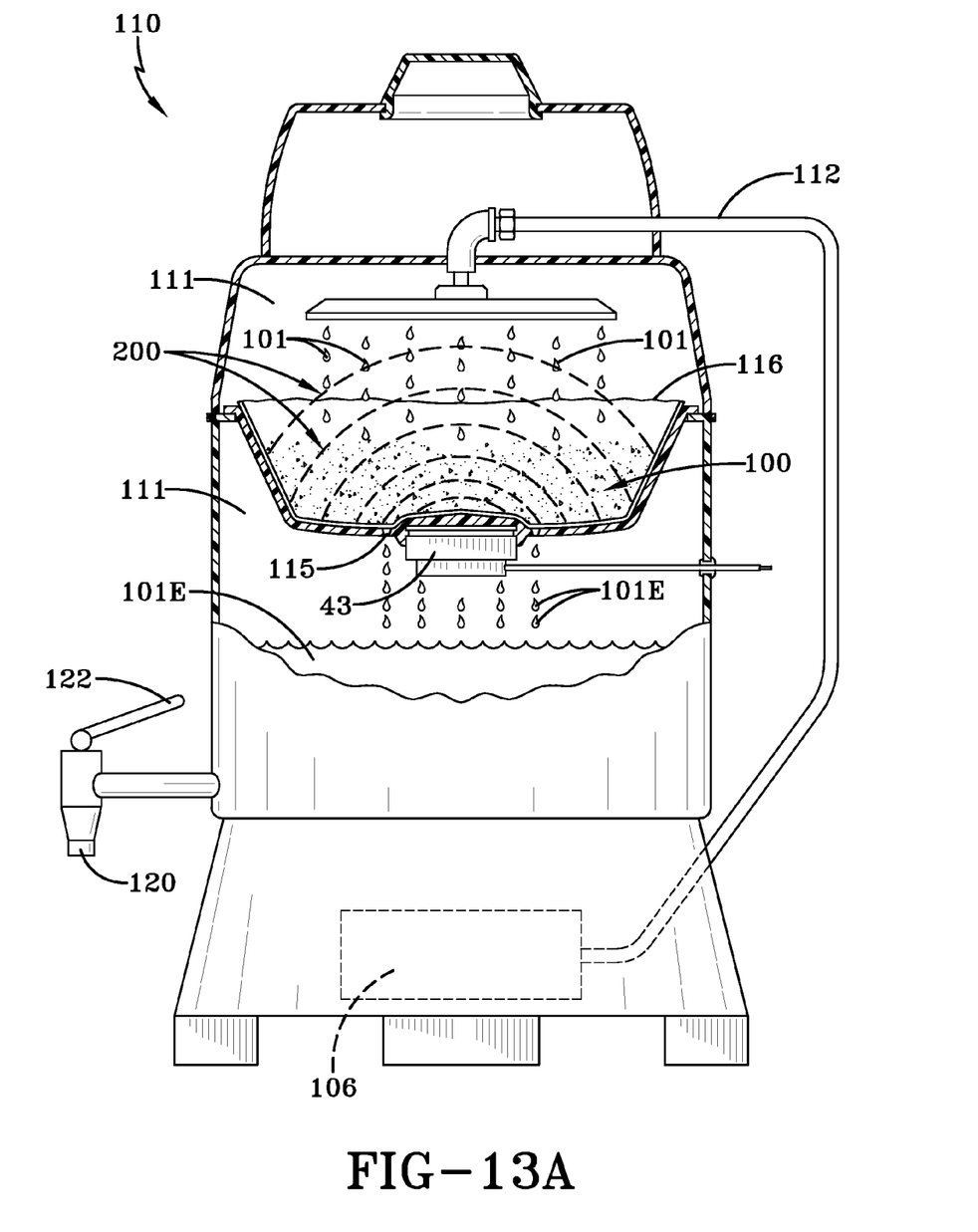
FIG. 13A shows cellular plant tissues being treated with shock waves being transmitted in an apparatus through a container or vat holding a quantity of plant cellular tissue in an upper portion of the apparatus, the tissue to be shock wave treated to enhance the percentage or quantity of extracted material removed from the plant cellular tissue to create a fluid with extract mixture.

With reference to FIG. 13A, a coffee brewing apparatus 110 has a container 111 or brewing vat illustrated adapted to brew coffee 100. The container 111 has a pipe inlet 112 or opening to receive fluid 101, preferably hot water. The water 101 is heated by a heating element 106 to a sufficient high temperature and then is passed through the pipe inlet 112 into a small internal container 114 holding prepared plant cellular tissue 100. The plant cellular tissue 100 in this case is a predetermined quantity of ground coffee 100.

Once the ground coffee 100 is completely immersed in water 101 a shock wave generator or electrode 43 is activated to emit a dosage of acoustic shock waves 200 to stimulate a cellular release of extract 100E into the fluid 101. Thereafter the fluid with extract mixture 101E is allowed to pass through one or more outlets 115 of the internal container 114 into a beverage holding portion of the container 111 shown as a lower portion of the apparatus 110. The transmission of shock waves 200 can occur initially once the grounds 100 are fully immersed and then stopped or can occur intermittently as more water 101 passes over and through the grounds 100 or the wave pattern 200 can be generated continuously until all the water 101 passes through the grounds 100.

As shown the finished beverage coffee can be withdrawn by the movement of the lever 122 which opens the spout 120 and pours into a cup for consumption.

Figure 13B:
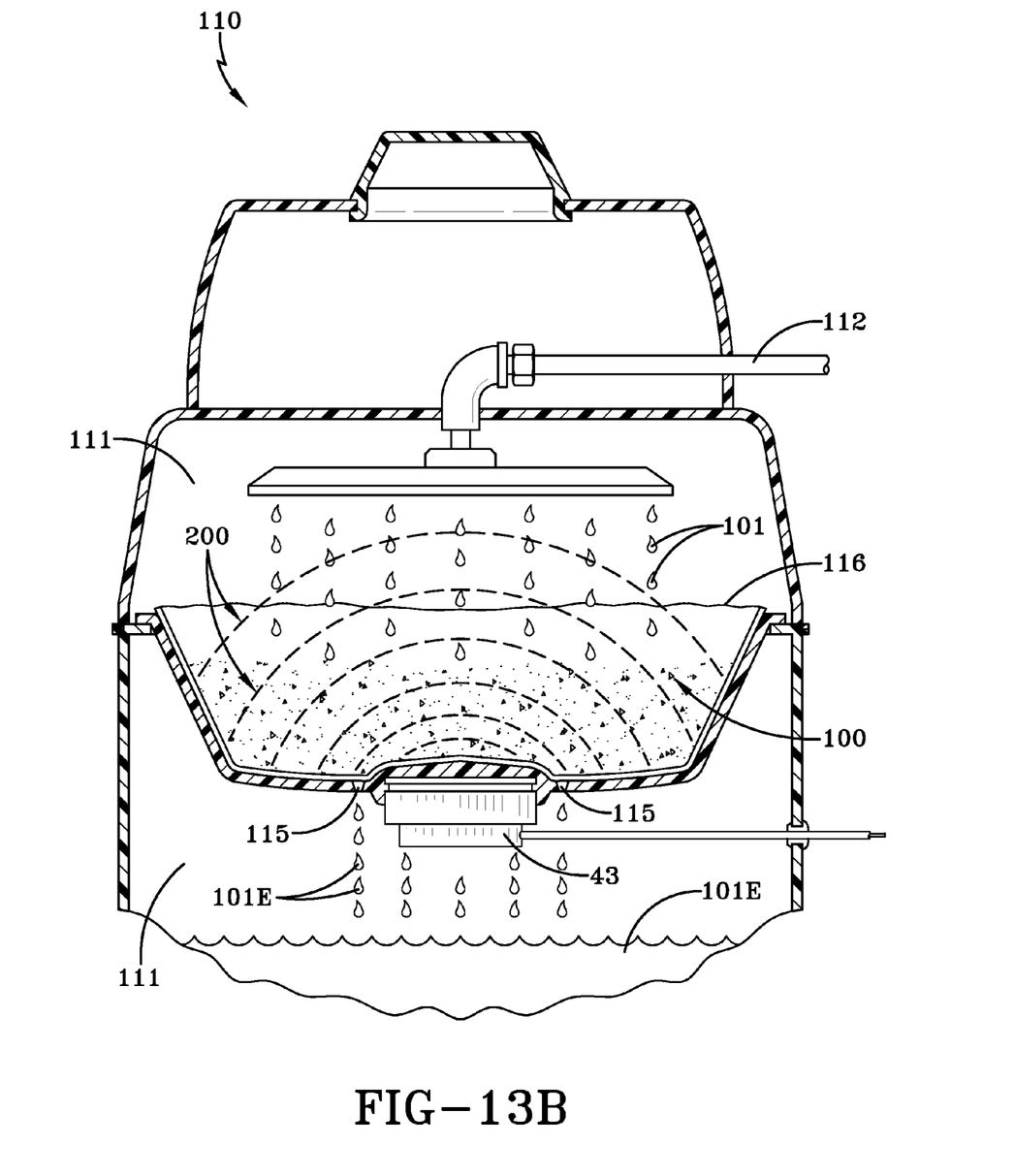
FIG. 13B shows an enlarged view of the upper portion of the apparatus of FIG. 13A.

With reference to FIG. 13B the electrode or shock wave generator device 43 is attached to the fluid filled internal container 114 and the transmission of the spark generated shock waves 200 are transmitted through the bottom of the internal container 114 into the fluid immersed coffee grounds 100. The location of the electrode 43 alternatively could be on a side or even the top of the internal container 114 as long as there are no air gaps or voids to impede the wave patterns 200. As the coffee 101E is being created, it can flow out of the one or more openings in the internal container 114 bottom as shown. Preferably the grounds 100 are retained in a screen or other type filtration device 116 as shown This example for coffee brewing can be adapted for other beverages such as tea, beer or other alcoholic beverages including, but not limited to wine production. Similarly the methods can be applied to increase plant derived extracts used in drug manufacturing.

The present invention employs the use of pressure pulses or shock waves to stimulate a cellular response stimulating a tissue cell release process that activates the more permeable tissue cell walls to initiate a systemic release of extractable plant matter.

In the pressure pulse or shock wave method of treating a plant tissue, a zygotic embryo or seed or somatic embryos of the plant or cultures of such embryos are positioned in a convenient orientation to permit the source of the emitted waves to most directly send the waves to the target site to initiate pressure pulse or shock wave stimulation of the target area or zone with minimal, preferably with little or no obstructing features in the path of the emitting source or lens. Assuming the treatment region is accessible through an open access region then the shock wave head 43 can be inserted and placed directly on or adjacent to the treatment region 200. Assuming the target area or site is within a projected area of the wave transmission, a single transmission dosage of wave energy may be used. The transmission dosage can be from a few seconds to 20 minutes or more dependent on the condition. Preferably the waves are generated from an unfocused or focused source. The unfocused waves can be divergent, planar or near planar and having a low pressure amplitude and density in the range of 0.00001 $mJ/mm^2$ to 1.0 $mJ/mm^2$ or less, most typically below 0.2 $mJ/mm^2$. The focused source preferably can use a diffusing lens or have a far-sight focus to minimize if not eliminate having the localized focus point within the treated plant cellular tissue. Preferably the focused shock waves are used at a similarly effective low energy transmission or alternatively can be at higher energy but wherein the tissue target site is disposed pre-convergence inward of the geometric focal point of the emitted wave transmission. In treating some hard to penetrate regions, the pressure pulse more preferably is a high energy target focused wave pattern which can effectively penetrate through outer structures prior to being dampened while still exposing the plant cells to activating pressure pulses or shock waves. This emitted energy preferably stimulates the plant cells with or without rupturing cellular membranes. The surrounding plant cells in the region treated are activated initiating a release mechanism response stimulating increases in extractable material.

These shock wave energy transmissions are effective in stimulating a cellular response and can be accomplished without creating the cavitation bubbles in the plant tissue of the target site when employed in other than site targeted high energy focused transmissions. This effectively insures the tissue or plant does not have to experience the sensation of cellular membrane rupturing so common in the higher energy focused wave forms having a focal point at or within the targeted treatment site when such cell rupturing causes adverse taste by products in certain beverages.

This method permits the lens or cover of the emitting shock wave source to impinge on the immersed plant tissue directly or through a transmission enhancing water or fluid medium during the pressure pulse or shock wave treatment. The treated area can withstand a far greater number of shock waves based on the selected energy level being emitted. For example at very low energy levels the stimulation exposure can be provided over prolonged periods as much as 20 minutes if so desired. At higher energy levels the treatment duration can be shortened to less than a minute, less than a second if so desired which can be emitted in an intermittent pulsed pattern if so desired. In some beverages the limiting factor in the selected treatment dosage is avoidance or minimization of tissue cell rupturing and other kinds of damage to the surrounding cells or tissue which can release unwanted tissue byproducts while still providing a stimulating cell activation or a cellular release or activation of proteins or functional fragments of the protein or other chemical composition that modulates factors such as extract yields. In less sensitive applications, cell rupturing is a desirable way to increase extract yield.

The underlying principle of these pressure pulse or shock wave therapy methods is to activate the treatment area directly and to stimulate the plant's own natural extract release capability. This is accomplished by deploying shock waves to stimulate cells in the surrounding plant tissue to activate a variety of responses. The acoustic shock waves transmit or trigger what appears to be a cellular communication throughout the entire anatomical structure, this activates a generalized cellular response at the treatment site, in particular, to release the materials into the extracted fluid. This is believed to be one of the reasons molecular stimulation can be conducted at threshold energies heretofore believed to be well below those commonly accepted as required. Accordingly not only can the energy intensity be reduced in some cases, but also the number of applied shock wave impulses can be lowered from several thousand to as few as one or more pulses and still yield a beneficial stimulating response. The key is to provide at least a sufficient amount of energy to activate cell reactions.

Ideally the present invention is best suited for large scale beverage making operations, but can be envisioned to be employed in small appliances such as residential coffee makers.

Nevertheless the use of such pressure pulses and acoustic shock waves can be very beneficial to plant yield production in terms of increasing the amount of extractable material per plant. The following pressure pulse/shock wave patterns are examples of some of the various forms of patterns that can be used in the present invention.

Figure 1A:
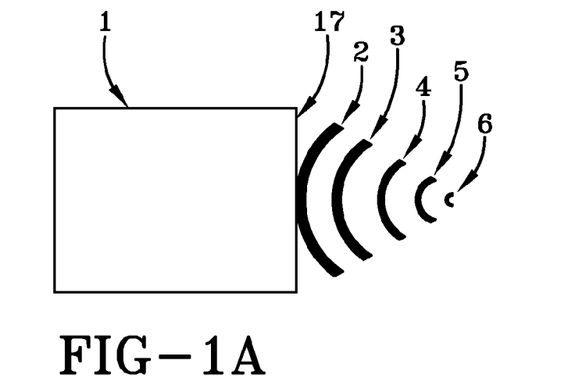
FIG. 1a is a simplified depiction of a pressure pulse/shock wave (PP/SW) generator with focusing wave characteristics.

FIG. 1a is a simplified depiction of the a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat plant cellular tissues such as leaves or seeds of plants. The plant tissue is generally located in or near the focal point which is located in or near position 6. At position 17 a water cushion or any other kind of exit window for the acoustical energy is located.

Figure 1B:
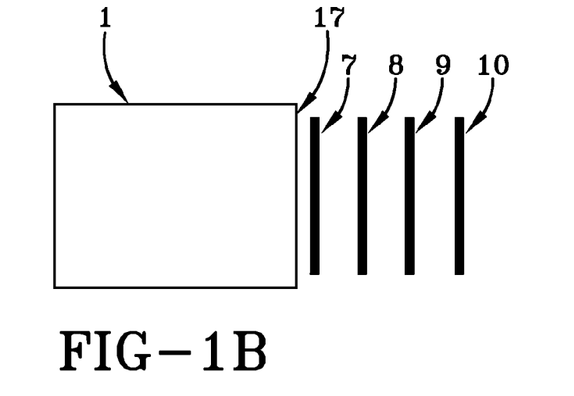
FIG. 1b is a simplified depiction of a pressure pulse/shock wave generator with plane wave characteristics.

FIG. 1b is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the plant tissue via a coupling media such as, e.g., hot water and their amplitudes will be attenuated with increasing distance from the exit window 17.

Figure 1C:
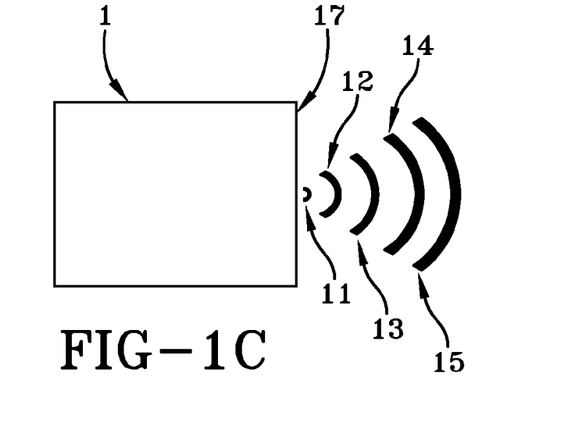
FIG. 1c is a simplified depiction of a pressure pulse/shock wave generator with divergent wave characteristics.

FIG. 1c is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 1c the pressure pulse source may be a point source, that is, the pressure pulse may be generated by an electrical discharge of an electrode under water between electrode tips. However, the pressure pulse may also be generated, for example, by an explosion, referred to as a ballistic pressure pulse. The divergent characteristics of the wave front may be a consequence of the mechanical setup shown in FIG. 2b.

Figure 2A:
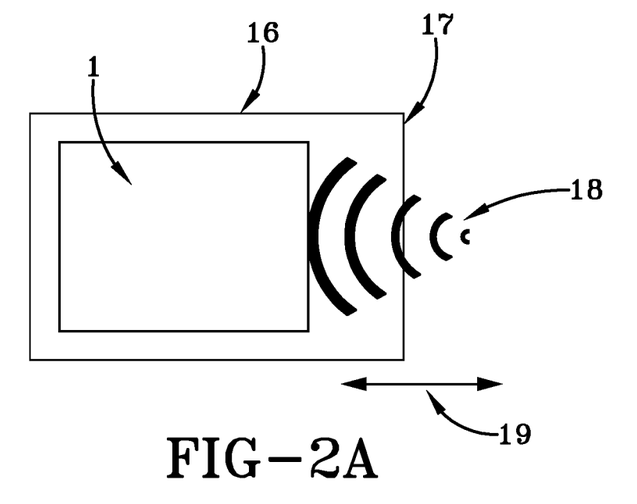
FIG. 2a is a simplified depiction of a pressure pulse/shock wave generator having an adjustable exit window along the pressure wave path. The exit window is shown in a focusing position.

FIG. 2a is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 2a is similar to FIG. 1a but depicts an outer housing (16) in which the acoustical pathway (pressure wave path) is located. In a preferred embodiment, this pathway is defined by especially treated water (for example, temperature controlled, conductivity and gas content adjusted water) and is within a water cushion or within a housing having a permeable membrane, which is acoustically favorable for the transmission of the acoustical pulses. In certain embodiments, a complete outer housing (16) around the pressure pulse/shock wave generator (1) may be adjusted by moving this housing (16) in relation to, e.g., the focusing element in the generator. However, as the person skilled in the art will appreciate, this is only one of many embodiments of the present invention. While the figure shows that the exit window (17) may be adjusted by a movement of the complete housing (16) relative to the focusing element, it is clear that a similar, if not the same, effect can be achieved by only moving the exit window, or, in the case of a water cushion, by filling more water in the volume between the focusing element and the cushion. FIG. 2a shows the situation in which the arrangement transmits focused pressure pulses.

Figure 2B:
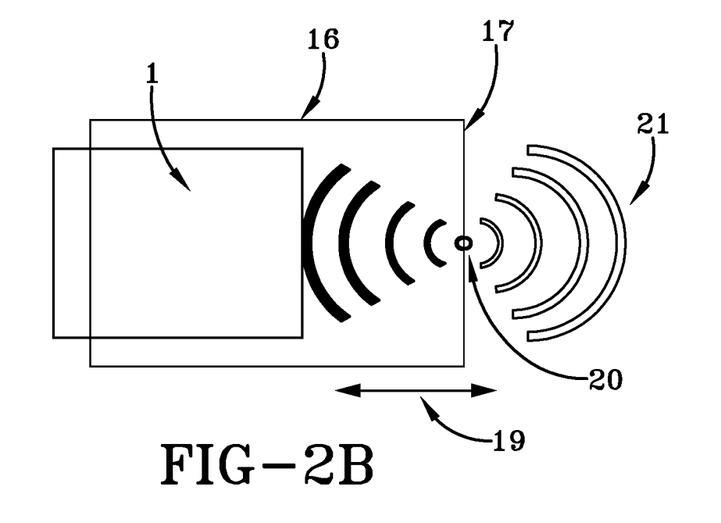
FIG. 2b is a simplified depiction of a pressure pulse/shock wave generator having an exit window along the pressure wave path. The exit window as shown is positioned at the highest energy divergent position.

FIG. 2b is a simplified depiction of the pressure pulse/shock wave generator (shock wave head) having an adjustable or exchangeable housing around the pressure wave path with the exit window 17 being in the highest energy divergent position. The configuration shown in FIG. 2b can, for example, be generated by moving the housing (16) including the exit window (17), or only the exit window (17) of a water cushion, towards the right (as shown in the Figure) to the second focus f2 (20) of the acoustic waves. In a preferred embodiment, the energy at the exit window will be maximal. Behind the focal point, the waves may be moving with divergent characteristics (21).

Figure 2C:
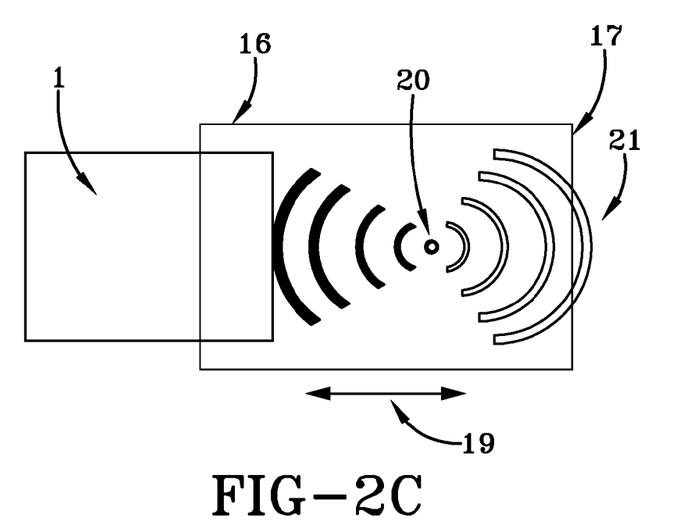
FIG. 2c is a simplified depiction of a pressure pulse/shock wave generator having an exit window along the pressure wave path. The exit window is shown at a low energy divergent position.

FIG. 2c is a simplified depiction of the pressure pulse/shock wave generator (shock wave head) having an adjustable or exchangeable housing around the pressure wave path in a low energy divergent position. The adjustable housing or water cushion is moved or expanded much beyond f2 position (20) so that highly divergent wave fronts with low energy density values are leaving the exit window (17) and may be coupled to a plant tissue. Thus, an appropriate adjustment can change the energy density of a wave front without changing its characteristic.

This apparatus may, in certain embodiments, be adjusted/modified/or the complete shock wave head or part of it may be exchanged so that the desired and/or optimal acoustic profile such as one having wave fronts with focused, planar, nearly plane, convergent or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combinational wave forms. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the present invention provides versatility, the person skilled in the art will appreciate that apparatuses that only produce waves having, for example, nearly plane characteristics, are less mechanically demanding and fulfill the requirements of many users.

As the person skilled in the art will also appreciate that embodiments shown in the drawings are independent of the generation principle and thus are valid for not only electrohydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a plant tissue is coupled via a fluid to the acoustic exit window (17), which can, for example, be an acoustic transparent membrane, a water cushion, a plastic plate or a metal plate.

Figure 3:
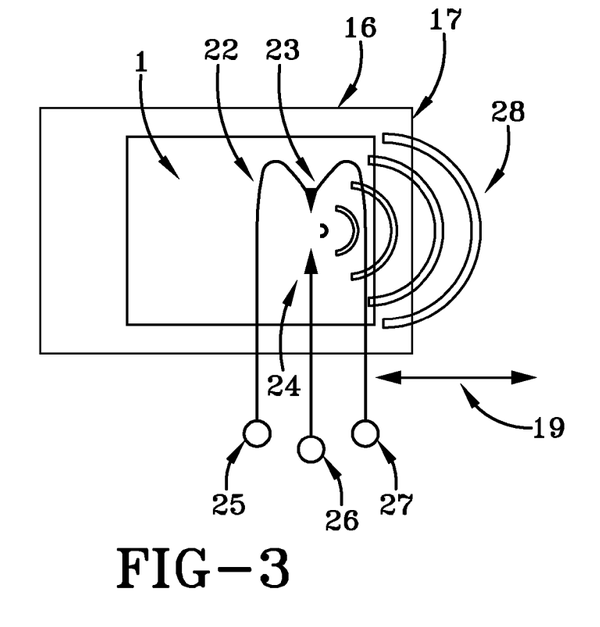
FIG. 3 is a simplified depiction of an electro-hydraulic pressure pulse/shock wave generator having no reflector or focusing element. Thus, the waves of the generator did not pass through a focusing element prior to exiting it.

FIG. 3 is a simplified depiction of the pressure pulse/shock wave apparatus having no focusing reflector or other focusing element. The generated waves emanate from the apparatus without coming into contact with any focusing elements. FIG. 3 shows, as an example, an electrode as a pressure pulse generating element producing divergent waves (28) behind the ignition point defined by a spark between the tips of the electrode (23, 24).

Figure 4A:
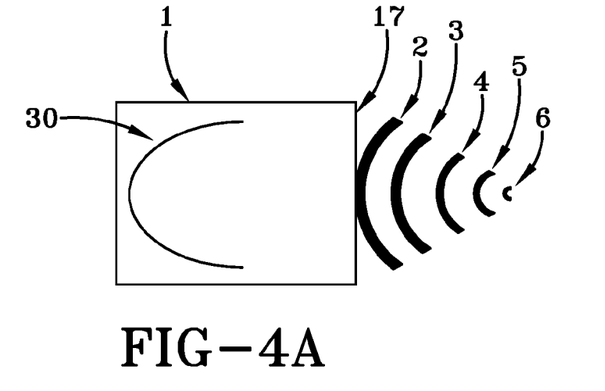
FIG. 4a is a simplified depiction of a pressure pulse/shock wave generator having a focusing element in the form of an ellipsoid. The waves generated are focused.

FIG. 4a is a simplified depiction of the pressure pulse/shock wave generator (shock wave head) having as focusing element an ellipsoid (30). Thus, the generated waves are focused at (6).

Figure 4B:
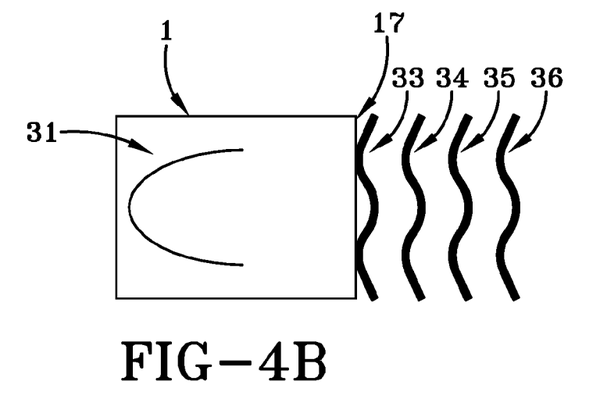
FIG. 4b is a simplified depiction of a pressure pulse/shock wave generator having a parabolic reflector element and generating waves that are disturbed plane.

FIG. 4b is a simplified depiction of the pressure pulse/shock wave generator (shock wave head) having as a focusing element an paraboloid ($y^2=2px$). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 4C:
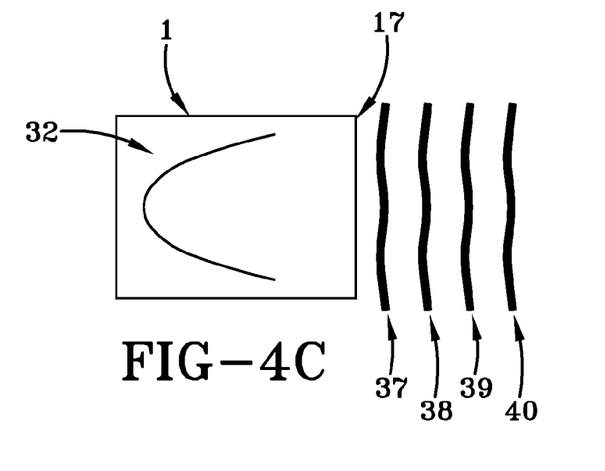
FIG. 4c is a simplified depiction of a pressure pulse/shock wave generator having a quasi parabolic reflector element (generalized paraboloid) and generating waves that are nearly plane/have nearly plane characteristics.

FIG. 4c is a simplified depiction of the pressure pulse/shock wave generator (shock wave head) having as a focusing element a generalized paraboloid ($y^n=2px$, with $1.2<n<2.8$ and $n\neq 2$). Thus, the characteristics of the wave fronts generated behind the exit window (37, 38, 39, and 40) are, compared to the wave fronts generated by a paraboloid ($y^2=2px$), less disturbed, that is, nearly plane (or nearly parallel or nearly even (37, 38, 39, 40)). Thus, conformational adjustments of a regular paraboloid ($y^2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y^2=2px$) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

Figure 4D:
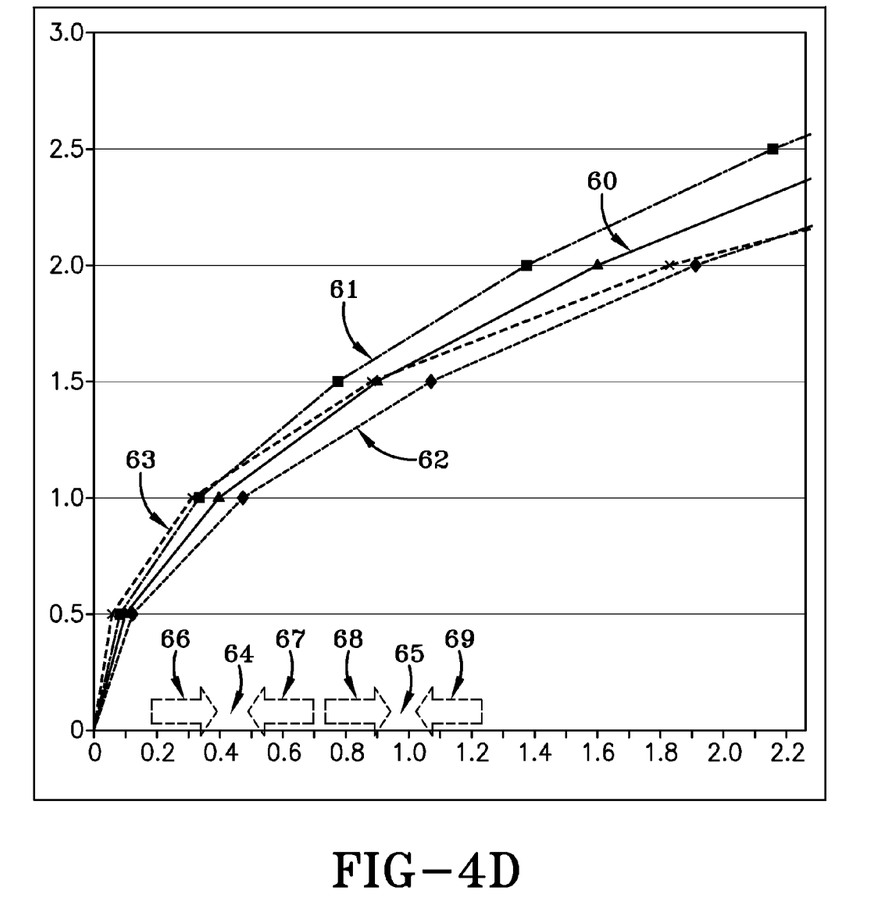
FIG. 4d is a simplified depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 4d shows sectional views of a number of paraboloids. Numeral 62 indicates a paraboloid of the shape $y^2=2px$ with p=0.9 as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicate by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62. This particular generalized paraboloid was generated by choosing a value of $n\neq 2$ and a p value of about 1.55 cm. The generalized paraboloid compensates for different p values that result from the electrode burn down and/or adjustment of the electrode tips.

Figure 5:
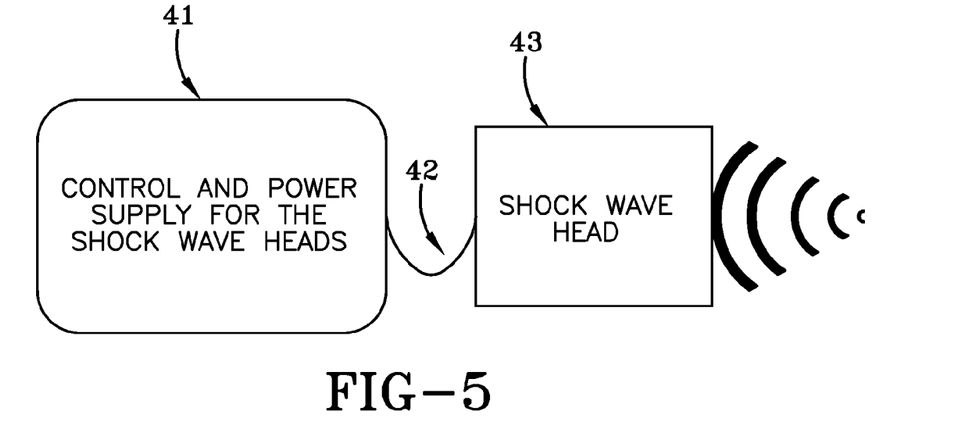
FIG. 5 is a simplified depiction of a pressure pulse/shock wave generator being connected to a control/power supply unit.

FIG. 5 is a simplified depiction of a set-up of the pressure pulse/shock wave generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 6:
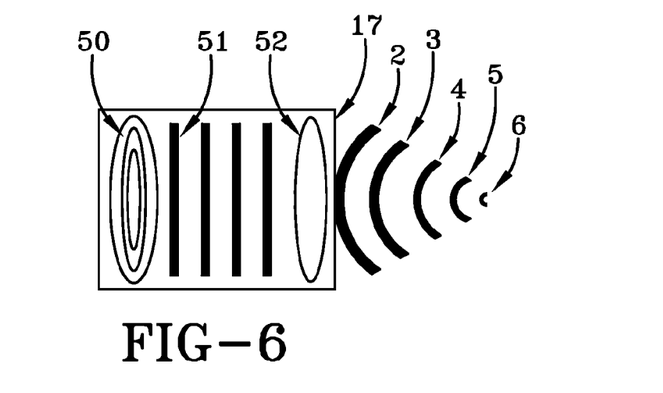
FIG. 6 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
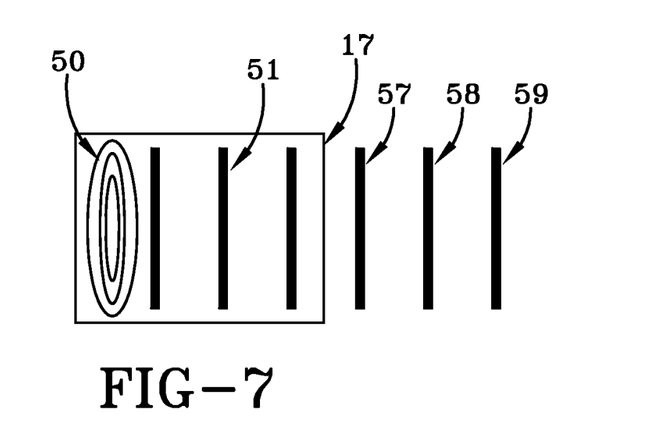
FIG. 7 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 8:
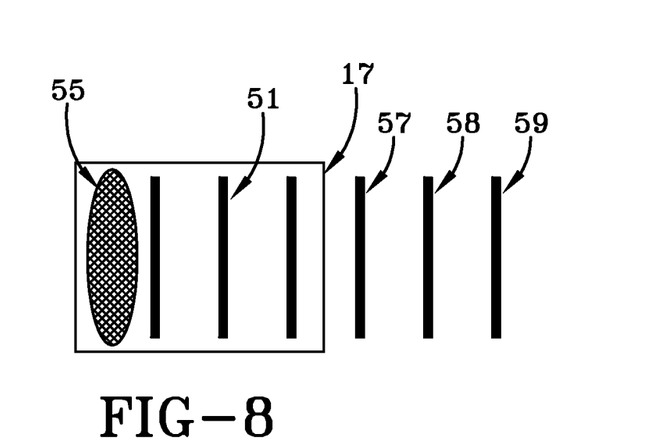
FIG. 8 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave generator (shock wave head) having an piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. 4a to 4c as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
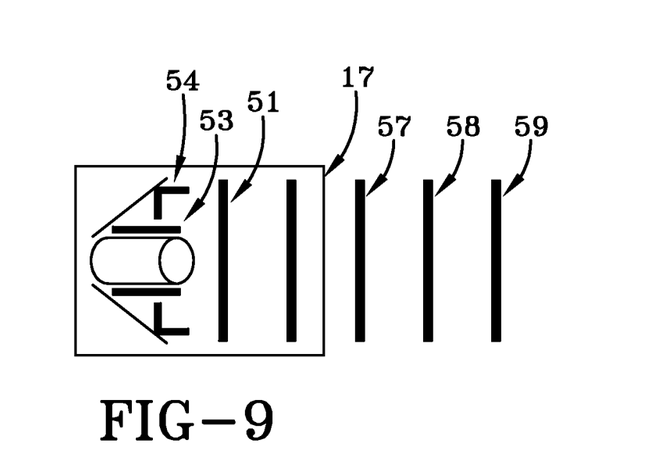
FIG. 9 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
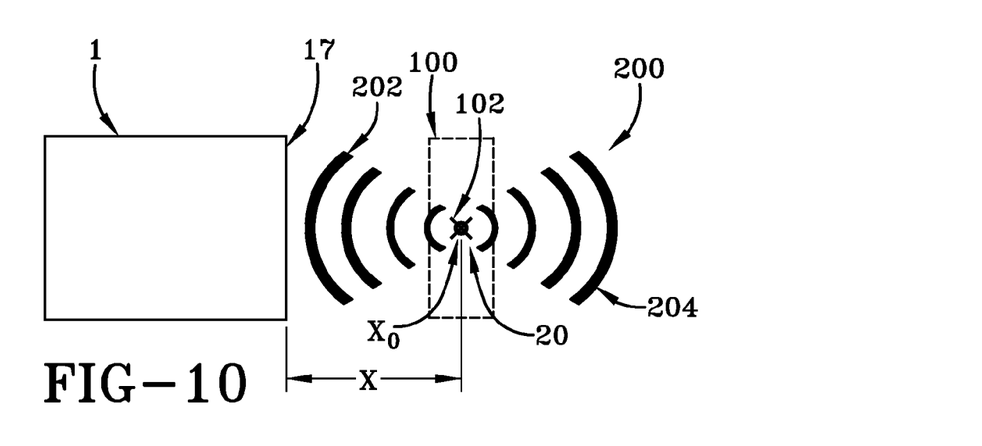
FIG. 10 is a simplified depiction of a pressure pulse/shock wave (PP/SW) generator with focusing wave characteristics shown focused with the focal point or geometrical focal volume being on a substance, the focus being targeted on the location $X_0$.
Figure 11:
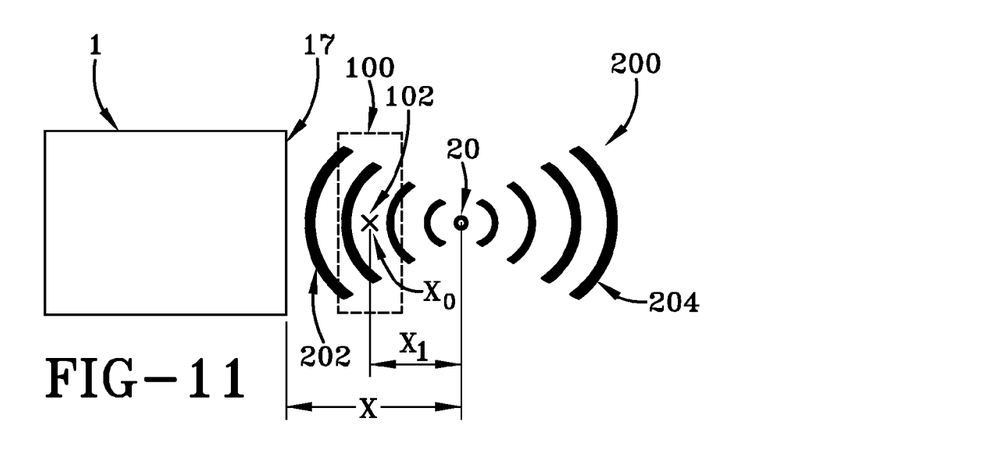
FIG. 11 is a simplified depiction of a pressure pulse/shock wave (PP/SW) generator with the focusing wave characteristics shown wherein the focus is located a distance X, from the location $X_0$ of a substance wherein the converging waves impinge the substance.
Figure 12:
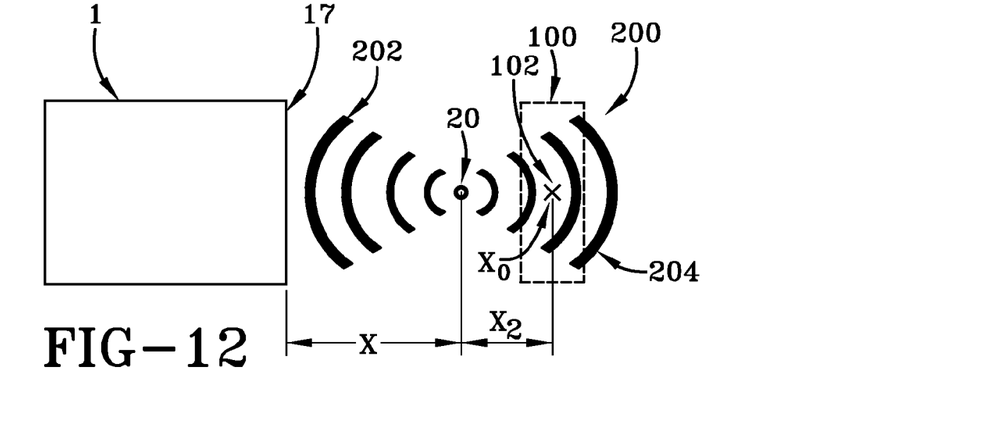
FIG. 12 is a simplified depiction of a pressure pulse/shock wave (PP/SW) generator with focusing wave characteristics shown wherein the focus is located a distance $X_2$ from the location $X_0$ wherein the emitted divergent waves impinge the substance.

With reference to FIGS. 10, 11 and 12 a schematic view of a shock wave generator or source 1 is shown emitting a shock wave front 200 from an exit window 17. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 1-9 generally.

With particular reference to FIG. 10 a plant tissue 100 is shown generally centered on the focal point or volume 20 at a location $X_0$ within the tissue 100. In this orientation the emitted waves are focused and thus are emitting a high intensity acoustic energy at the location $X_0$. This location $X_0$ can be anywhere within or on the tissue 100.

With reference to FIG. 11, the plant tissue 100 is shifted a distance X toward the generator or source 1. The tissue 100 at location $X_0$ being positioned a distance $X-X_1$ from the source 1. This insures the tissue 100 is impinged by converging waves 202 but removed from the focal point 20. When the tissue 100 is in this location the bombardment of converging waves 202 stimulates the cells activating the desired response as previously discussed.

With reference to FIG. 12, the plant cellular tissue 100 is shown shifted or located in the diverging wave portion 204 of the wave front 200. As shown $X_0$ is now at a distance $X_2$ from the focal point or geometric volume 20 located at a distance X from the source 1. Accordingly $X_0$ is located a distance $X+X_2$ from the source 1. As in FIG. 10 this region of diverging waves 204 can be used to stimulate the plant cellular tissue 100 which stimulates the cells to produce the desired effect or response increasing the quantity of material extracted from the cells.

As shown in FIGS. 1-12 the use of these various acoustic shock wave forms can be used separately or in combination to achieve the desired effect of stimulating extract yield.

The present invention provides an apparatus for an effective treatment of plant tissues, which benefit from high or low energy pressure pulse/shock waves having focused or unfocused, nearly plane, convergent or even divergent characteristics. With an unfocused wave having nearly plane, plane, convergent wave characteristic or even divergent wave characteristics, the energy density of the wave may be or may be adjusted to be so low that side effects including cellular membrane damage do not exist at all if so desired.

In certain embodiments, the apparatus of the present invention is able to produce waves having energy density values that are below 0.1 mJ/mm2 or even as low as 0.000 001 mJ/mm2. In a preferred embodiment, those low end values range between 0.1-0.001 mJ/mm2. With these low energy densities, side effects are reduced and the dose application is much more uniform. Additionally, the possibility of harming surface tissue is reduced when using an apparatus of the present invention that generates unfocused waves having planar, nearly plane, convergent or divergent characteristics and larger transmission areas compared to apparatuses using a focused shock wave source that need to be moved around to cover the treated area. The apparatus of the present invention also may allow the user to make more precise energy density adjustments than an apparatus generating only focused shock waves, which is generally limited in terms of lowering the energy output.

The treatment of the above mentioned plant tissue is believed to be a first time use of acoustic shock wave therapy in the manufacture of plant extracts or beverages. None of the work done to date has treated the above mentioned plant tissue with convergent, divergent, planar or near-planar acoustic unfocused shock waves of low energy or high energy focused shock waves in a transmission path from the emitting source lens or cover to the target site.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

The use of acoustic shock waves to plant tissue stimulates a cellular response of the treated tissues. This response activates otherwise dormant cells to increase the plant's cells to release more material to be extracted.

A further benefit of the use of acoustic shock waves is there are no known adverse indications when combined with the use of other process of manufacture. In fact the activation of the cells exposed to shock wave treatments only enhances cellular release of such extractable nutrients making them faster acting than when compared to non stimulated cells conventionally processed to yield an extract.

Another aspect of the present invention is the use of acoustic shock waves can be combined with organic food processing. The treatment does not require genetic alteration or manipulation to accelerate the otherwise improve extract yields of plant tissue as such the use of acoustic shock waves is compatible with organic farming practices as well as the new fields of genetic engineering.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

I claim:

1. An apparatus for increasing extracts taken from cellular plant tissue comprises:

a preparation container for holding the cellular plant tissue, the container having an inlet or opening to receive a fluid to wet the cellular plant tissue and take extracts from the cellular plant tissue to create a fluid with extracts mixture, and an outlet to pass the fluid with extracts mixture;

a holding vessel to receive the fluid with extracts; and an acoustic shock wave device for generating and transmitting shock waves to the wet cellular plant tissue to enhance release of extracts into the fluid wherein the acoustic shock wave has a very rapid pressure spike the amplitude of the positive part is above 0.1 MPa and the cycle time duration is from below a microsecond to a second with the rise time of the positive part of the pressure cycle being in the range of nanoseconds up to milliseconds, achieved in an extremely short duration accordingly as the wave approaches a cell it compresses the cell initially, thereafter the pressure of the wave drops in a slower fashion as it continues across the cell that tends to put tension on the cell wall as it relaxes from the sudden compressive rise in pressure causing the cell wall to rebound in a spring like fashion and stretches slightly increasing permeability, rapid bombardment of the acoustic waves in a pattern sequence, which first compresses then stretches, and creates a rapid cellular squeezing effect enhancing permeability into and out of the cell walls wherein the cellular plant tissue is completely immersed in fluid with no air gaps or voids to impede the acoustic wave patterns, the acoustic shock wave device for generating and transmitting being an electro-hydraulic, electromagnetic, piezoceramic or ballistic device wherein the pressure pulse source is a point source generated by an electrical discharge of an electrode, electromagnet or piezoceramic device under water or by an explosion to create acoustic shock waves exhibiting asymmetric ballistic pressure pulses for creating the rapid peak rise times.

2. The apparatus of claim 1 further comprises:
a heating element to heat the fluid prior to contacting the cellular plant tissue.

3. The apparatus of claim 1 further comprises:
a means to separate the fluid and extracts mixture from the cellular tissue wherein the cellular tissue is mechanically held as the fluid with extracts mixture passes to the holding vessel.

4. The apparatus of claim 1 wherein the acoustic shock wave device transmits the shock waves in a pattern covering a volumetric region of the held cellular tissue, the cellular tissue being immersed in the fluid.

5. The apparatus of claim 4 wherein the acoustic shock wave pattern is transmitted at least initially as the fluid passes through the cellular tissue.

6. The apparatus of claim 5 wherein the acoustic shock wave pattern is transmitted continuously as the fluid passes through the cellular tissue.

7. The apparatus of claim 5 wherein the transmission of the acoustic shock wave pattern is pulsed intermittently as the fluid passes through the cellular tissue.

8. The apparatus of claim 1 wherein the cellular plant tissue is ground coffee and the apparatus is coffee maker or coffee brewer.

9. The apparatus of claim 1 wherein the cellular plant tissue is coffee beans placed in a slurry to create a fluid with extract mixture to make an instant coffee product.

10. The apparatus of claim 1 wherein the cellular plant tissue is made of tea leaves and the apparatus is a tea maker.

11. The apparatus of claim 1 wherein the cellular plant tissue is one or more of the following; hops, barley, wheat, oats, soy beans or rice and the apparatus is used in brewing a beverage having an alcohol content.

12. The apparatus of claim 1 wherein the cellular plant tissue is used in the formulation of an extract for use in a drug or medicine composition.

\* \* \* \* \*